(12) United States Patent  (10) Patent No.: US 7,442,827 B2
Sugioka et al.  (45) Date of Patent: Oct. 28, 2008

(54) PROCESS FOR PRODUCING CYCLOPENTANONE-2, 3, 5-TRICARBOXYLIC ACID TRIESTER

(75) Inventors: Takashi Sugioka, Kurashiki (JP); Yoshimi Fukunaga, Tokyo (JP)

(73) Assignee: Kuraray Co., Ltd., Kurashiki-Shi, Okayama (JP)

( * ) Notice: Subject to any disclaimer, the term of this patent is extended or adjusted under 35 U.S.C. 154(b) by 0 days.

(21) Appl. No.: 11/587,822

(22) PCT Filed: May 10, 2005

(86) PCT No.: PCT/JP2005/008826

§ 371 (c)(1), (2), (4) Date: Oct. 27, 2006

(87) PCT Pub. No.: WO2005/115966

PCT Pub. Date: Dec. 8, 2005

(65) Prior Publication Data

US 2008/0027241 A1  Jan. 31, 2008

(30) Foreign Application Priority Data

Nov. 5, 2004  (JP) ............................... 2004-141147

(51) Int. Cl.
*C07C 69/74* (2006.01)
(52) U.S. Cl. .................................... 560/122
(58) Field of Classification Search ........................ None
See application file for complete search history.

(56) References Cited

U.S. PATENT DOCUMENTS 4,272,437 A  6/1981  Menard et al.

FOREIGN PATENT DOCUMENTS

JP  61-40245  2/1986

OTHER PUBLICATIONS

Noyce et al, Journal of Organic Chemistry, Studies of Configuration. V. The Preparation and Configuration of cis-3-Methoxycyclopentane carboxylic acid, 1959, 24, pp. 715-717.*
International Search Report and Written Opinion from PCT/JP2005/008826.
English Translation of International Preliminary Report on Patentability issued in corresponding International Application No. PCT/JP2005/008826 on Jan. 18, 2007, and attached Written Opinion; IB WIPO, Geneva, CH.
Vaughn, H., "The Stereochemical Relationship of (+)-3-N-Methylaminocyclopentene to (+)-Cyclopenten-3-OL", Doctoral Dissertation, Columbia University, 1955.
Noyce, Donald S. et al.: "Configuration V. Preparation and configuration of cis-3-methoxycyclopentanecarboxylic acid", Journal of Organic Chemistry, 24, 715-17 Coden: Joceah; ISSN: 0022-3293, 1959.
XP002473186, Database Accession No. 171243, J. Chem. Soc. vol. 101, 1912, pp. 892-912.
XP002473187, Database Accession No. 189543, J. Chem. Soc. vol. 101, 1912, pp. 892-912.
XP002473188, Database Accession No. 103933, J. Chem. Soc. vol. 101, 1912, pp. 892-912.
Supplemental European Search Report, European Patent Application No. 05 73 8573, dated Jan. 9, 2008.

* cited by examiner

*Primary Examiner*—Paul A Zucker
(74) *Attorney, Agent, or Firm*—Buchanan Ingersoll & Rooney PC

(57) ABSTRACT

The present invention provide a process that allows the industrially advantageous production of a cyclopentanone-2,3,5-tricarboxylic acid triester. Namely, the present invention provides a process for producing a cyclopentanone-2,3,5-tricarboxylic acid triester represented by the general formula (IV), characterized by comprising: (1) allowing an itaconic acid diester represented by the general formula (I) to react with a metal salt of malonic acid diester represented by the general formula (II) to obtain a reaction mixture containing an adduct represented by the general formula (III); and then (2) allowing said reaction mixture to react with an alcohol or a metal alkoxide, or a mixture thereof:

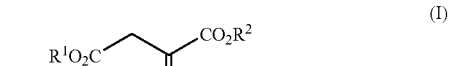

(I)

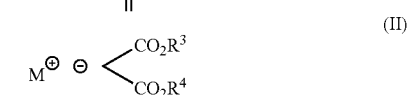

(II)

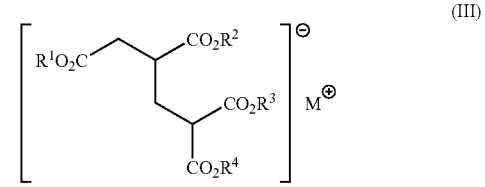

(III)

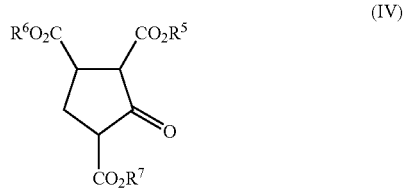

(IV)

wherein $R^1$, $R^2$, $R^3$, $R^4$, $R^5$, $R^6$, and $R^7$ each independently represents an alkyl group which may have a substituent, and M represents an alkali metal.

3 Claims, No Drawings

PROCESS FOR PRODUCING CYCLOPENTANONE-2, 3, 5-TRICARBOXYLIC ACID TRIESTER

TECHNICAL FIELD

The present invention relates to a process for producing a cyclopentanone-2,3,5-tricarboxylic acid triester. The cyclopentanone-2,3,5-tricarboxylic acid triester obtainable by the present invention is suitable for use as an intermediate in the synthesis of 3-oxocyclopentane-1-carboxylic acid or ester thereof, which is an intermediate of xanthine derivatives that are useful as adenosine antagonists (see JP-A-7-509492).

BACKGROUND ART

Conventionally, a method for producing cyclopentanone-2,3,5-tricarboxylic acid triester, which is comprised of allowing dimethyl itaconate to react with sodium salt of dimethyl malonate that is prepared from sodium hydride and dimethyl malonate, isolating a product (tetramethyl 1,1,3,4-butanetetracarboxylate) from resulting reaction mixture by purification with distillation after neutralizing with an acid, and then cyclizing the product in the presence of not less than one equivalent of sodium methoxide, and isolating a target compound from resultant reaction mixture after neutralizing with an acid, has been known (see U.S. Pat. No. 4,272,437, columns 361-362).

The above-mentioned conventional process requires twice neutralization treatment including that after the cyclization step, further purification with distillation, and the like, because of isolating a reaction product of dimethyl itaconate and sodium salt of dimethyl malonate once. These make steps very vexatious and complicated. Moreover, 1.07 molar equivalents of sodium methoxide is used as a base in the cyclization step, thereby the waste discharged from the neutralization treatment necessarily increases leading to a heavy load to the environment. Furthermore, yield of a cyclopentanone-2,3,5-tricarboxylic acid trimethylester is as low as 50% based on dimethylitaconate. Consequently, these problems make the conventional process unsuited to industrial applications, and the process has a room to be improved.

Accordingly, an object of the present invention is to provide a process that allows the industrially advantageous production of a cyclopentanone-2,3,5-tricarboxylic acid triester with a simple and convenient after-treatment and less waste.

The present inventors have diligently researched in order to solve the problems of the conventional process, and discovered as a result that by allowing an itaconic acid diester to react with a metal salt of malonic acid diester, and allowing obtained reaction mixture to react with an alcohol or a metal alkoxide, or a mixture-thereof, conversion to the desired cyclopentanone-2,3,5-tricarboxylic acid triester is enabled without isolating an adduct of an itaconic acid diester and a metal salt of malonic acid diester, or the adduct with neutralized form, which are intermediates, and accomplished the present invention.

DISCLOSURE OF THE INVENTION

Namely, the present invention provides a process for producing a cyclopentanone-2,3,5-tricarboxylic acid triester represented by the general formula (IV):

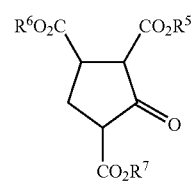

wherein $R^5$, $R^6$, and $R^7$ each independently represents an alkyl group which may have a substituent (hereinafter referred to as cyclopentanone-2,3,5-tricarboxylic acid triester (IV)); characterized by comprising:

(1) allowing an itaconic acid diester represented by the general formula (I):

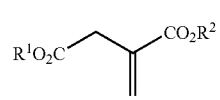

wherein $R^1$ and $R^2$ each independently represents an alkyl group which may have a substituent (hereinafter referred to as itaconic acid diester (I)); to react with a metal salt of malonic acid diester represented by the general formula (II)

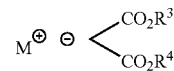

wherein $R^3$ and $R^4$ each independently represents an alkyl group which may have a substituent, and M represents an alkali metal (hereinafter referred to as metal salt of malonic acid diester (II)]; to obtain a reaction mixture containing an adduct represented by the general formula (III):

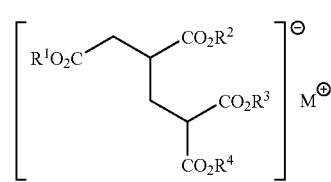

wherein $R^1$, $R^2$, $R^3$, $R^4$, and M are as defined above (hereinafter referred to as adduct (III)); (hereinafter this step may be referred to as step (1)) and then (2) allowing said reaction mixture to react with an alcohol or a metal alkoxide, or a mixture thereof (hereinafter, this step may be referred to as step (2)).

Moreover, in a preferable embodiment, a mixture of an alcohol and a metal alkoxide is used in the above step (2), and furthermore, an amount of the metal alkoxide used is not more than one molar equivalent with respect to itaconic acid diester (I).

According to the present invention, a process that allows the industrially advantageous production of a cyclopentanone-2,3,5-tricarboxylic acid triester can be produced in high yield, with a easy after-treatment and less waste is provided.

BEST MODE FOR CARRYING OUT THE INVENTION

The alkyl group that $R^1$, $R^2$, $R^3$, $R^4$, $R^5$, $R^6$ and $R^7$ each independently represents in the above general formulae is preferably a linear, branched or cyclic alkyl group having 1 to 12 carbon atoms, such as methyl group, ethyl group, propyl group, isopropyl group, butyl group, hexyl group, octyl group, dodecyl group, cyclopentyl group, cyclohexyl group, and the like.

The alkali metal that M represents is such as lithium, sodium, potassium, and the like.

First, step (1), namely, a step in which itaconic acid diester (I) and metal salt of malonic acid diester (II) are reacted, will be described.

The metal salt of malonic acid diester (II) can be simply and conveniently prepared by allowing a base containing an alkali metal to react with a corresponding malonic acid diester. Examples of the base include alkali metal hydrides such as lithium hydride and sodium hydride; alkali metal hydroxides such as lithium hydroxide, sodium hydroxide, and potassium hydroxide; alkali metal alkoxides such as sodium methoxide, sodium ethoxide, potassium methoxide, and potassium ethoxide; and organic alkali metal compounds such as methyllithium and n-butyllithium; and the like. Of these, when an alkali metal hydroxide or an alkali metal alkoxide is used as the base, it is preferably to remove generated water or an alcohol out of the reaction system before carrying out the reaction of itaconic acid diester (I) with metal salt of malonic acid diester (II), because said water or an alcohol may cause side reaction in said reaction.

An amount of itaconic acid diester (I) used maybe selected as appropriate in consideration with reaction efficiency and conversion of itaconic acid diester (I), but is generally in a range of 0.5 to 10 equivalents, preferably in a range of 0.5 to 2 equivalents with respect to metal salt of malonic acid diester (II).

The reaction is preferably carried out in the presence of a solvent. There are no particular restrictions on the solvent as long as it does not adversely affect the reaction, and examples of such solvent include aliphatic hydrocarbons such as hexane, heptane and octane; aromatic hydrocarbons such as benzene, toluene, xylene, ethylbenzene and mesitylene; and ethers such as tetrahydrofuran, diethyl ether, diisopropyl ether, tert-butyl methyl ether, 1,2-dimethoxyethane, 1,4-dioxane and diethyleneglycol dimethyl ether; and the like. These solvents may be used singly or in a mixture of two or more. Of these, from the viewpoint of ease of treatment in carrying out the neutralization treatment after completion of all reactions, it is preferred to use a solvent which is immiscible in water, and it is more preferred to use toluene or diisopropyl ether.

Reaction temperature is generally selected from a range of −20 to 100° C.

The step (1) can be carried out, for example, by adding itaconic acid diester (I) or a mixture of itaconic acid diester (I) and a solvent to a mixture containing metal salt of malonic acid diester (II) and a solvent, or by adding metal salt of malonic acid diester (II) to a mixture of itaconic acid diester (I) and a solvent. Time required for the addition is not particularly restricted, but generally in a range of 0.5 to 10 hours from the viewpoint of controlling reaction temperature, because the step (1) is an exothermal reaction. Reaction time is not particularly restricted, but generally in a range of 0.5 to 20 hours.

Although, the reaction mixture obtained in the step (1) contains adduct (III), the present invention is characterized by subjecting the reaction mixture to the step (2) described below without isolating adduct (III) with neutralized form from adduct (III), to obtain a cyclopentanone-2,3,5-tricarboxylic acid triester.

Secondly, step (2), namely, a step in which the above-mentioned reaction mixture obtained in the step (1) is reacted with an alcohol or a metal alkoxide, or a mixture thereof, will be described.

The step (2) can be carried out by adding an alcohol to the reaction mixture obtained in the above step (1). Examples of the alcohol include methanol, ethanol, 1-propanol, 2-propanol, 1-butanol, 2-butanol, 2-methyl-2-propanol, 1-pentanol, 1-hexanol, 1-octanol and the like. These alcohols may be used singly or in a mixture of two or more. An amount of alcohol used is not particularly restricted, and when there are many amount of the alcohol used, the reaction rate can be enhanced generally. However, the amount may be selected appropriately from the viewpoints of solubility of the reaction mixture, reaction temperature, reaction time, ease of isolation treatment for the reaction product or the like, and generally in a range of 0.1 to 5 times by mole with respect to itaconic acid diester (I).

In the present invention, by further using a metal alkoxide in addition to an alcohol, reaction rate of the step (2) can be enhanced. Moreover, even by using only a metal alkoxide, the step (2) can be carried out. Examples of such metal alkoxide include alkali metal alkoxides such as lithium methoxide, lithium ethoxide, lithium tert-butoxide, sodium methoxide, sodium ethoxide, sodium tert-butoxide, potassium methoxide, potassium ethoxide and potassium tert-butoxide; alkaline-earth metal alkoxides such as magnesium dimethoxide, magnesium diethoxide, calcium dimethoxide and calcium diethoxide; and the like. These metal alkoxides may be used singly or in a mixture of two or more. An amount of the metal alkoxide used may be selected appropriately from the viewpoints of reaction temperature, reaction time, and reaction solvent or the like, but is preferably in a range of 0.01 to 1 molar equivalent, and more preferably in a range of 0.05 to 0.2 molar equivalent with respect to itaconic acid diester (I), from the viewpoint of reducing amount of a waste in the neutralization treatment.

When an alcohol and a metal alkoxide are used as a mixture, mixing ratio thereof is not particularly restricted, and an amount of the metal alkoxide used in the alcohol is preferably not more than one molar equivalent with respect to itaconic acid diester (I). In addition, when an alcohol and a metal alkoxide are used as a mixture, a kind of the alcohol is allowed to be different from alcohol source forming the metal alkoxide.

The reaction is preferably carried out in the presence of a solvent. As the solvent, preferably the solvent used in the step. (I) continues to be used as it is, but another solvent may be added freshly. There are no particular restrictions on the solvent added freshly as long as it does not adversely affect the reaction, and examples of the solvent include aliphatic hydrocarbons such as hexane, heptane and octane; aromatic hydrocarbons such as benzene, toluene, xylene, ethylbenzene and mesitylene; ethers such as tetrahydrofuran, diethyl ether, diisopropyl ether, tert-butyl methyl ether, 1,2-dimethoxyethane, 1,4-dioxane and diethyleneglycol dimethyl ether; and the like.

Reaction temperature is generally selected from a range of 0° C. to a temperature at which reaction mixture is refluxed. Reaction time is not particularly restricted, but generally in a range of 1 to 30 hours.

The step (2) may be carried out by adding an alcohol or a metal alkoxide, or a mixture thereof to the reaction mixture obtained in the above step (1) at the predetermined temperature.

Cyclopentanone-2,3,5-tricarboxylic acid triester (IV) obtained in this manner can be isolated and purified by means ordinarily employed in the isolation and purification of an organic compound. For example, an acidic aqueous solution is added to the reaction mixture to neutralize. After the aqueous layer is separated, the organic layer is concentrated, and the resultant crude product is purified by column chromatography, recrystallization, distillation or the like.

EXAMPLES

The present invention will now be described in detail with reference to Examples and are not intended to limit the scope of the present invention any way.

Example 1

Toluene (600 ml) and 60% sodium hydride (30 g, 748 mmol) were placed in a reaction vessel having a capacity of 2 L. Dimethyl malonate (96 g, 726 mmol) was added dropwise to the solution over one hour with the internal temperature kept below 30° C. After completion of the dropping, a solution obtained by dissolving dimethyl itaconate (113 g, 712 mmol) in toluene (400 ml) was added dropwise over one hour with the internal temperature kept below 30° C. Subsequently, after the mixture was reacted for 3 hours with the internal temperature kept at 25° C., 28% sodium methoxide solution in methanol (14.0 g, 71 mmol) was then added thereto, and the mixture was heated at the internal temperature of 70° C. for 5 hours. The resultant reaction mixture was cooled to a temperature not higher than 20° C., and 20% sulfuric acid aqueous solution (300 ml) was added dropwise over 10 minutes with the internal temperature kept below 30° C. The reaction mixture was allowed to stand for separation. After confirming that a pH of an aqueous layer was not higher than 3, an organic layer was separated. The organic layer was washed with saturated sodium hydrogen carbonate aqueous solution (100ml), concentrated under reduced pressure, and the residue was purified using silica gel column chromatography to obtain 156.1 g of cyclopentanone-2,3,5-tricarboxylic acid trimethylester (yield: 85%).

Example 2

The similar reactions and after-treatments were carried out as in Example 1, except that a powdery sodium methoxide (3.92 g, 71 mmol) was used instead of 28% sodium methoxide solution in methanol (14.0 g, 71 mmol) and the reaction time after completion of adding the sodium methoxide was changed to 20 hours, to obtain 132.2 g of cyclopentanone-2,3,5-tricarboxylic acid trimethylester (yield: 72%).

Example 3

The similar reactions and after-treatments were carried out as in Example 1, except that an amount of 60% sodiumhydride used is changed from 30 g to 28 g (700 mmol), methanol (100 ml) was used instead of 28% sodium methoxide solution in methanol (14.0 g, 71 mmol) and the reaction time was changed from 5 hours to 10 hours, to obtain 148.8 g of cyclopentanone-2,3,5-tricarboxylic acid trimethylester (yield: 81%).

INDUSTRIAL APPLICABILITY

Cyclopentanone-2,3,5-tricarboxylic acid triester obtainable by the present invention is suitable for use as an intermediate in the synthesis of 3-oxocyclopentane-1-carboxylic acid or ester thereof, which is an intermediate of xanthine derivatives that are useful as adenosine antagonists (see JP-A-7-509492).

What is claimed is:

1. A process for producing a cyclopentanone-2,3,5-tricarboxylic acid triester represented by the general formula (IV):

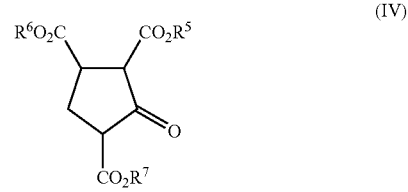

wherein $R^5$, $R^6$, and $R^7$ each independently represents an alkyl group which may have a substituent; the process comprising:

(1) allowing an itaconic acid diester represented by the general formula (I):

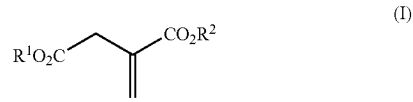

wherein $R^1$ and $R^2$ each independently represents an alkyl group which may have a substituent; to react with a metal salt of malonic acid diester represented by the general formula (II):

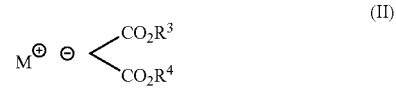

wherein $R^3$ and $R^4$ each independently represents an alkyl group which may have a substituent, and M represents an alkali metal; to obtain a reaction mixture containing an adduct represented by the general formula (III):

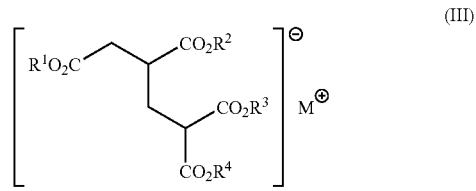

wherein $R^1$, $R^2$, $R^3$, $R^4$, and M are as defined above; and then (2) allowing said reaction mixture without isolating the adduct (III) from said reaction mixture to react with an alcohol and a metal alkoxide mixture to form the cyclopentanone-2,3,5-tricarboxylic acid triester represented by the general formula (IV).

2. The process for producing a cyclopentanone-2,3,5-tricarboxylic acid triester according to claim 1, wherein an amount of the metal alkoxide used is not more than one molar equivalent with respect to an itaconic acid diester represented by the general formula (I):

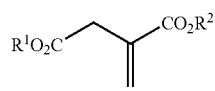 (I)

wherein $R^1$ and $R^2$ each independently represents an alkyl group which may have a substituent.

3. The process for producing a cyclopentanone-2,3,5-tricarboxylic acid triester according to claim 1, wherein an amount of the metal alkoxide is in a range of 0.01 to 1 molar equivalent with respect to the itaconic acid diester.

* * * * *